(12) United States Patent
Sato et al.

(10) Patent No.: US 7,825,284 B2
(45) Date of Patent: Nov. 2, 2010

(54) PROCESS FOR THE PRODUCTION OF CARDANOL

(75) Inventors: Setsuo Sato, São José dos Campos (BR); Wanderson Bueno de Almeida, São José dos Campos (BR); Arnaldo Ferreira Filho, Jacarei (BR); Ramiro Carielo Bueno, Jacarei (BR)

(73) Assignee: Cognis IP Management GmbH, Duesseldorf (DE)

( * ) Notice: Subject to any disclaimer, the term of this patent is extended or adjusted under 35 U.S.C. 154(b) by 341 days.

(21) Appl. No.: 11/911,347

(22) PCT Filed: Apr. 5, 2006

(86) PCT No.: PCT/EP2006/003100

§ 371 (c)(1),
(2), (4) Date: Jun. 9, 2008

(87) PCT Pub. No.: WO2006/108545

PCT Pub. Date: Oct. 19, 2006

(65) Prior Publication Data

US 2009/0281355 A1    Nov. 12, 2009

(30) Foreign Application Priority Data

Apr. 14, 2005    (DE) .................. 10 2005 017 126

(51) Int. Cl.
*C07C 39/10* (2006.01)
*C07C 39/00* (2006.01)

(52) U.S. Cl. ...................................... 568/763; 568/716

(58) Field of Classification Search ................ None
See application file for complete search history.

(56) References Cited

U.S. PATENT DOCUMENTS

| 4,352,944 A | 10/1982 | Tyman et al. ............... 568/766 |
| 6,229,054 B1 | 5/2001 | Dai et al. ..................... 568/630 |
| 6,262,148 B1 | 7/2001 | Cheng et al. ................ 523/458 |

FOREIGN PATENT DOCUMENTS

| GB | 2066820 | 7/1981 |
| GB | 2152925 | 8/1985 |
| GB | 2262525 | 6/1993 |

OTHER PUBLICATIONS

Shishen Dat el al. "Phenalkamines: Multipurpose Epoxy Curing Agent"; Cardolite Corporation, Newark, New Jersey, USA; Reprint EPI-ERF Conference, Sep. 1994.

*Primary Examiner*—Daniel M Sullivan
*Assistant Examiner*—Clinton Brooks

(57) ABSTRACT

A process for the production of a color-stable composition containing cardanol and cardol including (a) subjecting crude, cashew nutshell liquid to distillation to obtain a distillate: (b) reacting the distillate with boric acid to obtain a reaction mixture; and (c) subjecting the reaction mixture to distillation is provided. A method for the production of color-stable phenalkamines including (a) subjecting crude, cashew nutshell liquid to distillation to obtain a distillate; (b) reacting the distillate with boric acid to obtain a reaction mixture; (c) subjecting the reaction mixture to distillation to obtain a main fraction; and (d) reacting the main fraction with an aliphatic amine and formaldehyde to form a color-stable phenalkamine is also provided.

10 Claims, No Drawings

PROCESS FOR THE PRODUCTION OF CARDANOL

CROSS-REFERENCE TO RELATED APPLICATIONS

This application is the national phase under 35 U.S.C. §371 of PCT International Application No. PCT/EP2006/003100 which has an International filing date of Apr. 5, 2006, which designated the United States of America and which claims priority on German Patent Application number DE 102005017126.5 filed Apr. 14, 2005, the entire contents of each of which are hereby incorporated herein by reference.

BACKGROUND OF THE INVENTION

1. Field of the Invention

This invention relates generally to an improved process for the production of cardanol from cashew nutshell liquid (CNSL). The process is distinguished by the fact that the cardanol thus obtainable contains fewer secondary products than the usual, commercially available cardanol.

2. Background Information

Phenalkamines are still a relatively young class of epoxy resin curing agents. They are products of the reaction (condensation products) of cardanol (I), which, chemically, is a $C_{15}$ alkylphenol and a major constituent of the oil obtainable from cashew nutshells (CNSL=cashew nut shell liquid), with aliphatic (primary or secondary) amines and formaldehyde.

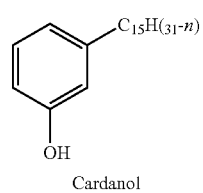

Cardanol (I)

Information on the class of phenalkamines can be found in the following publication: Zhishen Dal et al., "Phenalkamines: Multipurpose Epoxy Curing Agent"; Cardolite Corporation, Newark, N.J., USA; Reprint SPI-ERF Conference, September 1994.

It is known that crude CNSL predominantly contains a compound known as anacardic acid (II). The distillation of CNSL in the presence of acid gives a composition which mainly contains cardanol and, as a secondary product, cardol (III), cf. for example U.S. Pat. Nos. 6,262,148 and 6,229,054. This is consistent with applicants' own studies, according to which the distillation of crude CNSL gives a composition which mainly contains cardanol and, as a secondary product, cardol plus small quantities of 2-methyl cardol and anacardic acid.

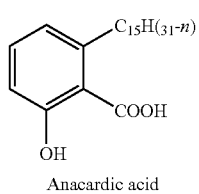

Anacardic acid (II)

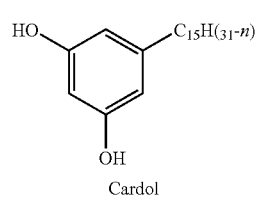

Cardol (III)

The cardanol/cardol mixture obtained in this way has three technical disadvantages:

- Its production by distillation from crude CNSL involves losses of value because part of the cardanol is lost through polymerization so that, ultimately, the yield of cardanol in the distillate is only 50-60%.
- The initially pale yellowish cardanol/cardol mixture changes during storage, rapidly turning brown in color. This unwanted change in color is attributed to the presence of cardol.
- Products ensuing from the cardanol/cardol mixture also undergo unwanted changes in color during storage.

It has also been proposed to improve the color stability of cardanol/cardol mixtures by reducing the cardol content by special measures. To this end, it has been proposed first to react the cardol present in the CNSL largely selectively with aldehydes, amines or bases and hydroxides of alkali and alkaline earth metals and then to distil off the unreacted cardanol. Particulars of these processes for the production of cardanol with improved color stability can be found in GB-A-2,152,925, GB-A-2,066,820 and U.S. Pat. No. 4,352,944.

SUMMARY OF THE INVENTION

Briefly described, according to an aspect of the invention, a process for the production of a color-stable composition containing cardanol and cardol includes the steps of (a) subjecting crude, cashew nutshell liquid to distillation to obtain a distillate; (b) reacting the distillate obtained in step (a) with boric acid to obtain a reaction mixture; and (c) subjecting the reaction mixture obtained in step (b) to distillation.

According to another aspect of the invention, a method for the production of color-stable phenalkamines includes the steps of: (a) subjecting crude, cashew nutshell liquid to distillation to obtain a distillate; (b) reacting the distillate obtained in step (a) with boric acid to obtain a reaction mixture; (c) subjecting the reaction mixture obtained in step (b) to distillation to obtain a main fraction; and (d) reacting the main fraction with an aliphatic amine and formaldehyde to form a color-stable phenalkamine.

DETAILED DESCRIPTION OF THE INVENTION

The present invention provides a process for the production of color-stable cardanol. In addition, products derived from the cardanol produced by this process, particularly phenalkamines, are color-stable.

It has surprisingly been found that this can be achieved by subjecting crude CNSL to a special chemical treatment and subsequent distillation. In a preferred embodiment the distillate may then be subjected to a further treatment with chemical adsorbents.

The key steps of the process according to the invention are as follows:

1. Distillation, more particularly short-path distillation, of crude CNSL

2. Reaction of the distillate ("crude cardanol") with boric acid
3. Distillation of the reaction mixture of step 2, more particularly short-path distillation.

If desired, the main fraction of step 3 may be after-treated with small quantities of adsorbents and/or reducing agents. This is an optional measure.

The present invention relates to a process for the production of a color-stable composition containing cardanol and cardol, in which
1. crude CNSL (cashew shell nut liquid) is first subjected to distillation, more particularly short-path distillation,
2. the distillate obtained is reacted with boric acid and
3. a distillation is then carried out, low-boiling fractions first being removed and the main fraction representing the target product (the color-stable cardanov cardol composition).

The CNSL used in the process according to the invention is of natural origin. It is obtained by extraction from the shells of cashew nuts (i.e. nuts of the tree *Anacardium occidentale*) and can vary in its composition. Typically, it contains 60-65% cardanol, 2-10% cardol, 10-15% oligomers/polymers and 0-2% 2-methylcardanol and anacardic acid.

The process according to the invention provides a color-stable composition containing cardanol and cardol. This composition is not only color-stable in storage, the phenalkamines produced from it are also. In addition, the composition is distinguished by the fact that it has better dermatological compatibility than known commercially available products, so that handling and transportation are safer.

In a preferred embodiment, the main fraction of step 3 of the process according to the invention is after-treated with small quantities of adsorbents and/or reducing agents. A further increase in color stability is achieved by the use of adsorbents and/or reducing agents.

The following observations apply to the three abovementioned compulsory steps of the process according to the invention:

Step 1 comprises substantially removing oligomers (with molecular weights of 1,000 to 3,000) from the crude CNSL. This is done by distillation, even simple short-path distillation leading to excellent results. During this distillation, ca. 15-20% by weight of the CNSL is removed in the form of the oligomers mentioned. Short-path distillation is the preferred distillation method. It is associated with rapid completion of the process, so that secondary processes, such as polymerization or oxidation, are suppressed as far as possible or minimized. The short-path distillation is preferably carried out as follows: first runnings of 2 to 5% by weight (based on the CNSL used) are removed at temperatures of 150-200° C. and pressures of 1-5 mmHg, followed by a main fraction at temperatures of 220-260° C. and pressures of 1 to 5 mmHg. This main fraction—the actual distillate from step 1—is also referred to as crude cardanol.

In step 2, the distillate from step 1 is reacted with boric acid ($H_3BO_3$). In this way, the dihydric phenols present are converted into the corresponding boric acid esters. The molar ratio of crude cardanol from step 1 to boric acid is preferably adjusted to a value of 3:0.07 to 3:0.1. The reaction temperature is preferably adjusted to a value of 120 to 150° C. The reaction time is preferably between 30 and 90 minutes and, more particularly, around 1 hour. Water of reaction formed is preferably removed (stripped off) continuously from the system. Boric acid is preferably used in a stoichiometric quantity in relation to the cardols present in the crude cardanol from step 1.

The mixture from step 3 is then subjected to a distillation in which the low-boiling constituents are removed and the relatively high molecular weight boric acid esters remain in the residue. The distillation may be carried out by any of the methods known to the expert. In one embodiment, it is carried out in vacuo under the conditions of a short-path distillation or a conventional fractional distillation. In another embodiment, first runnings of around 2-5% by weight are removed, more particularly at 180-210° C./1-5 mmHg. The main fraction, which represents the desired target product according to the invention and which accumulates at 220 to 260° C./1-5 mmHg, contains around 80 to 90% of the mixture from step 2 of the process. The high-boiling constituents mentioned remain in the residue.

Whereas steps 1 to 3 are essential to the process according to the invention, step 4 is optional. Any impurities still present are largely removed in step 4. Basically, there are no limitations as to the nature of the adsorbents or reducing agents used. Examples of suitable reducing agents are sodium hydrosulfite ($Na_2S_2O_4$), sodium metabisulfite ($Na_2S_2O_5$), sodium borohydride ($NaBH_4$), lithium aluminium hydride ($LiAlH_4$), tin chloride ($SnCl_2$) or magnesium silicate. Suitable adsorbents are, for example, magnesium silicate or chemically equivalent compounds. The quantity of adsorbents or reducing agents used may be kept to a minimum. Quantities of 0.1 to 5% by weight (based on the main fraction obtained in step 3) are preferably used, quantities of around 1% by weight being particularly preferred.

The present invention also relates to the use of cardanol-containing mixtures obtainable by the process according to the invention for the production of color-stable phenalkamines.

EXAMPLES

Example 1

Process According to the Invention

Step 1:
1250 g/h of CNSL (from Resibras/Brazil) were fed continuously through a short-path evaporator unit equipped with a pre-evaporator system running at 250° C./1 mmHg and 190° C./5 mmHg, respectively. Conditions: first runnings in the pre-evaporator=63 g/h; main fraction 940 g/h.

Step 2:
5000 g of the distillate from the main fraction ("crude cardanol") were reacted with 5.9 g of boric acid for 1 hour at 160° C. Water of esterification water was removed continuously during the reaction.

Step 3:
The material from step 2 was fed continuously (940 g/h) through a short-path evaporator unit equipped with a pre-evaporator system running at 250° C./1 mmHg and 200° C./3 mmHg, respectively. Conditions: first runnings in the pre-evaporator=60 g/h; main fraction=796 g/h. The distillate from the pre-evaporator was recycled to the raw material of step 1 (mixing with CNSL).

Step 4:
796 g of the main fraction of step 3 were then mixed with 7 g of magnesium silicate. The mixture was stirred for 30 mins. at 50° C. and then filtered through a suitable filter, such as a Sparkler or press filter. A pure and color-stable cardanol was obtained in this way.

Example 2

Determination of Color Stability

The product obtained in accordance with Example 1 was subsequently stored for 60 days at 20° C. Samples were taken from time to time and their color values (Gardner color values) were determined. A commercially available cardanol was also subjected to the long-term storage test and its color values were determined in the same way. The results are set out in Table 1. The row beginning with "Example 1" contains the Gardner color values of the product of Example 1 according to the invention according to the invention. The row beginning with "Standard" contains the Gardner color values of a commercially available cardanol (product of Palmer International, Inc., USA).

TABLE 1

|  | 1 Day | 7 Days | 15 Days | 30 Days | 45 Days | 60 Days |
|---|---|---|---|---|---|---|
| Example 1 | 2.3 | 2.5 | 2.9 | 3.2 | 3.3 | 4.2 |
| Standard | 3 | 6 | 12 | 15 | 17 | n.d. | n.d. = not determined

It can be seen that the product according to the invention is far superior to the commercially available standard.

In addition, it was found that phenalkamines produced from the product of Example 1, amines (especially diethylamine) and formaldehyde were also distinguished by color stability.

What is claimed is:

1. A process for the production of a color-stable composition containing cardanol and cardol, comprising the steps of:
   (a) subjecting crude, cashew nutshell liquid to distillation to obtain a distillate;
   (b) reacting the distillate obtained in step (a) with boric acid to obtain a reaction mixture; and
   (c) subjecting the reaction mixture obtained in step (b) to distillation.

2. The process according to claim 1, wherein step (a) comprises short-path distillation.

3. The process according to claim 2, wherein step (a) further comprises: removing first runnings of 1 to 5% by weight, based on the weight of the crude, cashew nutshell liquid of step (a), during the short-path distillation.

4. The process according to claim 1, wherein step (b) comprises adding boric acid in a stoichiometric quantity in relation to the cardols present in the distillate of step (a).

5. The process according to claim 4, wherein step (b) further comprises the step of continuously removing water formed by the reaction.

6. The process according to claim 1, wherein step (c) comprises short-path distillation.

7. The process according to claim 6, wherein step (c) further comprises: removing first runnings of 1 to 5% by weight, based on the weight of the reaction mixture.

8. The process according to claim 1, further comprising the step of treating the product obtained by the process with adsorbents and/or reducing agents.

9. The process according to claim 8, further comprising the step of filtration, after the step of treating.

10. A method for the production of color-stable phenalkamines, comprising the steps of:
   (a) subjecting crude, cashew nutshell liquid to distillation to obtain a distillate;
   (b) reacting the distillate obtained in step (a) with boric acid to obtain a reaction mixture;
   (c) subjecting the reaction mixture obtained in step (b) to distillation to obtain a main fraction; and
   (d) reacting the main fraction with an aliphatic amine and formaldehyde to form a color-stable phenalkamine.

* * * * *